United States Patent
Plihalova et al.

(10) Patent No.: US 12,378,247 B2
(45) Date of Patent: Aug. 5, 2025

(54) MESYLATE SALT OF PARA-TOPOLIN, COMPOSITIONS CONTAINING SAID SALT AND USE THEREOF

(71) Applicant: USTAV EXPERIMENTALNI BOTANIKY AV CR, V. V. I., Prague (CZ)

(72) Inventors: Lucie Plihalova, Olomouc (CZ); Marek Zatloukal, Sumperk (CZ); Karel Dolezal, Hlubocky (CZ); Miroslav Strnad, Olomouc (CZ); Jan Walla, Olomouc (CZ); Jiri Voller, Brno (CZ)

(73) Assignee: USTAV EXPERIMENTALNI BOTANIKY AV CR, V. V. I., Prague (CZ)

( * ) Notice: Subject to any disclaimer, the term of this patent is extended or adjusted under 35 U.S.C. 154(b) by 252 days.

(21) Appl. No.: 17/613,221

(22) PCT Filed: Aug. 22, 2020

(86) PCT No.: PCT/CZ2020/050061
§ 371 (c)(1),
(2) Date: Nov. 22, 2021

(87) PCT Pub. No.: WO2021/233486
PCT Pub. Date: Nov. 25, 2021

(65) Prior Publication Data
US 2023/0055908 A1    Feb. 23, 2023

(30) Foreign Application Priority Data
May 17, 2020    (CS) ................ PV 2020-277

(51) Int. Cl.
*C07D 473/34*    (2006.01)

(52) U.S. Cl.
CPC ........ *C07D 473/34* (2013.01); *C07B 2200/13* (2013.01)

(58) Field of Classification Search
CPC .. C07D 473/34; C07B 2200/13; A61K 31/52; A61P 17/00; A61P 25/00; A61P 29/00; A61P 35/00; A61P 37/00; A61P 17/06; A61P 17/10; A61P 19/02; A61P 25/04; A61P 37/06
See application file for complete search history.

(56) References Cited

U.S. PATENT DOCUMENTS 8,552,013 B2    10/2013    Popa et al.
2008/0014227 A1*   1/2008    Popa .................. A61P 25/28
                                                   514/263.1

OTHER PUBLICATIONS

Gupta D, Bhatia D, Dave V, Sutariya V, Varghese Gupta S. Salts of Therapeutic Agents: Chemical, Physicochemical, and Biological Considerations. Molecules. Jul. 14, 2018;23(7):1719. doi: 10.3390/molecules23071719. PMID: 30011904; PMCID: PMC6100526. (Year: 2018).*

Berge SM, Bighley LD, Monkhouse DC. Pharmaceutical salts. J Pharm Sci. Jan. 1977;66(1):1-19. doi: 10.1002/jps.2600660104. PMID: 833720. (Year: 1977).*

Trávníček Z, Matiková-Malarová M, Stěpánková K. 6-(2-Chloro-benzyl-amino)purinium tetra-chlorido(dimethyl sulfoxide-κO)(nitrosyl-κN)ruthenate(III) monohydrate. Acta Crystallogr Sect E Struct Rep Online. 2007;64(Pt 4):m545-6. doi: 10.1107/S1600536808006673. PMID: 21202003; PMCID: PMC2961006. (Year: 2007).*

Kadlecova Alena et al: "Natural plant hormones cytokinins increase stress resistance and longevity ofCaenorhabditis elegans", Biogerontology, Kluwer, Amsterdam, NL, vol. 19, No. 2, Dec. 18, 2017 (Dec. 18, 2017), pp. 109-120, XP036446144,ISSN: 1389-5729, DOI:10.1007/S10522-017-9742-4, retrieved Nov. 15, 2021.

Tang Chunlan et al: "Identification, characterization andin vitroneuroprotection of N6-(4-hydroxybenzyl) adenine riboside and its metabolites", Phytochemistry Letters, Elsevier, Amsterdam, NL, vol. 20, May 4, 2017 (May 4, 2017), pp. 146-150, XP085112564,ISSN: 1874-3900, DOI:10.1016/J.PHYTOL.2017.04.035.

International Search Report and Written Opinion for corresponding PCT application No. PCT/CZ2020/050061, mailed Oct. 12, 2020.

* cited by examiner

*Primary Examiner* — Joseph K McKane
*Assistant Examiner* — Anna Grace Kuckla
(74) *Attorney, Agent, or Firm* — Notaro, Michalos & Zaccaria P.C.

(57) ABSTRACT

A para-topolin mesylate salt and its crystalline form is disclosed. Cosmetic and therapeutic applications, and compositions containing this compound, are also disclosed. Mesylate salt of para-topolin has a wide range of biological activities, including antioxidative, anti-inflammatory, anti-senescent and anti-aging while showing low toxicity and excellent solubility.

14 Claims, 4 Drawing Sheets

MESYLATE SALT OF PARA-TOPOLIN, COMPOSITIONS CONTAINING SAID SALT AND USE THEREOF

FIELD OF ART

The invention relates to 6-(4-hydroxybenzylamino) purine (para-topolin) mesylate (methylsulphonate), its use in cosmetic and medicinal applications, and to compositions containing this salt.

BACKGROUND ART

Cytokinins are plant signal compounds (phytohormones) that play a central role in the regulation of the plant cell cycle and numerous developmental processes. Cytokinins were discovered by F. Skoog, C. Miller and co-workers during the 1950s as factors that promote cell division (cytokinesis). The first cytokinin discovered was an adenine derivative named kinetin (6-furfurylaminopurine), which was isolated as a DNA degradation product. The first common natural cytokinin identified was purified from immature maize kernels and named zeatin (chemical name: 6-(4-hydroxy-3-methylbut-2-enylamino) purine). Several other cytokinins with related structures are known today. Cytokinins have a broad spectrum of biological effects.

6-(4-Hydroxybenzylamino) purine (para-topolin, pT) is a cytokinin, whose cosmetic and therapeutic properties are known, e.g. from U.S. Pat. No. 8,552,013. Unfortunately, pT is practically insoluble in water but has a high cell membrane permeability. Low water solubility and slow dissolution rate are often limiting factors responsible for the low bioavailability of pharmaceutical/cosmetical compounds, limiting their applicability. Despite the long known fact that para-topolin has anti-aging compound properties, no successful para-topolin treatment regimens have been, or are, employed in the treatment of skin. One plausible explanation for this is probably the poor solubility and poor bioavailability as well as the rapid phase II metabolism of para-topolin in its known form.

It is an object of the present invention to provide a water-soluble form of para-topolin, particularly suitable for cosmetic and medical use.

DISCLOSURE OF THE INVENTION

This invention provides 6-(4-hydroxybenzylamino) purine (para-topolin) mesylate (methylsulphonate). It is a salt that consists of protonized 6-(4-hydroxybenzylamino) purine cation, so-called 6-(4-hydroxybenzylamino) purinium, and methylsuphonate (so-called mesylate) as an anion. The compound is represented by general formula I,

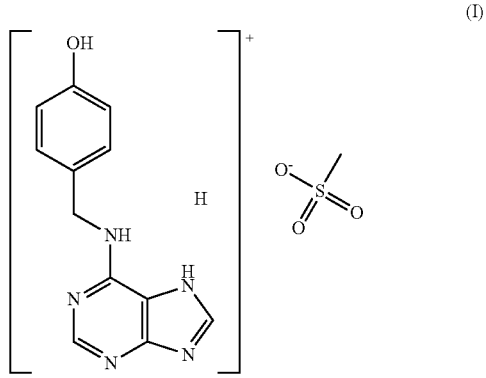

(I)

In one embodiment, the invention provides a crystalline form of para-topolin mesylate. This compound crystallizes in a triclinic crystal system with P-1 space group.

Preferably, the invention relates to a crystalline form of para-topolin mesylate having characteristic peaks in the X-ray powder diffraction pattern measured by CuKα radiation: 9.0; 9.2; 17.0; 17.9; 18.1; 22.3; 22.4; 24.1; 26.4±0.2° 2-theta. More preferably, the crystalline form may have further characteristic peaks: 13.6; 15.6; 16.3; 16.7; 19.8; 25.7; 27.2±0.2° 2-theta.

In the present invention, upon re-solution of the single crystal structure, it was found that the crystalline form of para-topolin mesylate salt has the general formula $C_{13}H_{15}N_5O_4S$ with a protonated purine based p-topoline cation and a mesylate anion. Centrosymmetric dimers of the asymmetric unit are interconnected by a series of intermolecular hydrogen bonds, which occur mainly between the protonated cation and the mesylate anion. This affects the torsion angles and together with the network of hydrogen bonds contributes to excellent water solubility.

The para-topolin mesylate salt according to the present invention has a wide range of biological activities, including antioxidant, antiinflammatory, anti-senescent, antiaging, and pro-differentiation activities, which are especially useful in pharmaceutical and cosmetic applications, e.g. to treat skin diseases or to improve skin condition. The compounds according to the present invention have minimal or zero toxicity.

The object of the present invention also para-topolin mesylate for use in vivo in cellular defence, tissue defence or whole organism defence against oxidative or electrophilic stress, for use for detoxication and elimination of reactive oxidants and electrophils, for use as antioxidant for inhibition of peroxidation of lipids, proteins or DNA in animals or plants.

Furthermore, the object of the present invention is in vitro use of para-topolin mesylate for protection of cells, organelles or organs against oxidative or electrophilic stress, use for detoxication and elimination of reactive oxidants and electrophils, and use as antioxidant for inhibition of peroxidation of lipids, proteins or DNA in plant or animal cells, organelles or organs.

An object of the present invention is para-topolin mesylate for use as a medicament. It can be used in treatment of animals (in veterinary medicine) and humans (in human medicine).

Preferably, the invention provides para-topolin mesylate for use in the treatment or improvement of skin diseases or skin conditions such as acne, erythema, or redness.

Preferably, the invention provides para-topolin mesylate for use as antineurodegenerative drug, or for use in method of suppression of immunostimulation or inflammation, such as in the treatment of arthritis or suppression of transplant rejection or in providing pain relief.

Preferably, this invention provides para-topolin mesylate for use in prevention and treatment of diseases involving oxidative stress in skin, in particular diseases selected from skin cancer and psoriasis, fibrotic disorders such as scleroderma, graft versus host disease (GVHD), hypertrophic scars, nephrogenic systemic fibrosis (NSF), allergic eczema, toxic eczema, atopic dermatitis, lichen planus, hyperpigmentation, herpes simplex lesions, ichthyosis, papilloma, Bowen's disease, seborrheic keratoses, actinic keratoses, basal and squamous cell carcinoma.

This invention further provides use of para-topolin mesylateuse in cosmetics as cosmetically active agent. Cosmetic use of this compound includes rejuvenation of cells and tissues, stimulation of cell proliferation and/or differentiation, inhibition, delay or reduction of adverse effects of aging or of senescence of cell and tissues, especially epidermal cells such as keratinocytes or fibroblasts. The cosmetic uses also include improving the overall appearance and condition of the mammalian skin, in particular human skin. Thus, cosmetic skin conditions such as acne, erythrema, redness and the like can be improved or treated.

This invention also provides use of para-topolin mesylate for in vitro rejuvenation of cells and tissues, stimulation of cell proliferation, morphogenesis and/or differentiation, or inhibiting of cell aging and tissue aging, e.g. in tissue cultures of keratinocytes and fibroblasts.

As used herein, reduction, inhibition or delaying of the adverse effects of aging of mammalian cells means that the development of the morphological changes that normally occur with aging in normal mammalian cells in vitro or in vivo is slowed down, reversed, and/or stopped. The adverse effects of aging also include age-related changes in gene expression and protein biosynthesis. The ameliorative effects referred to herein are those showing increasing the growth rate or total proliferative capacity of the cells treated. Inhibition, reduction or delaying the adverse effects of aging on the cells may be detected as a delay or reversal of the onset of age-related morphological and phenotypical changes that normally occur with aging of the cells. Age-related changes in vivo include changes in mammalian tissues, such as development of, or increase in number or depth of wrinkles or lines, sagging skin, discolorations, blotchiness, leathery and/or yellowed areas of the skin, undesirable cosmetic appearance of the skin as well as the associated changes in the structural and functional integrity of the tissue.

The present invention further provides cosmetic and/or pharmaceutical compositions comprising para-topolin mesylate and at least one cosmetically and/or pharmaceutically acceptable carrier.

Para-topolin mesylate or a composition comprising para-topolin mesylate are applied systemically or locally. A common way of application is topical; but injection, oral, or other appropriate forms of administration may be considered as well at the discretion of the physician. When used in cell or tissue cultures, para-topolin mesylate or preparations containing it are applied on the treated cells or tissues.

Pharmaceutical and Cosmetic Compositions

Suitable routes for systemic administration are oral, inhalation, injection (intravascular, intramuscular, subcutaneous), buccal, sublingual and nasal. For example, topical administration is possible in the form of creams, ointments, lotions, solutions, eye and ear drops, in the form of vaginal preparations and rectal suppositories. Solutions, creams and ointments are preferred for the treatment of scalp and skin diseases. The preferred route of administration depends on the condition of the patient and the site of the disease, in addition to other considerations known to the clinician.

Therapeutic compositions generally comprise about 1% to about 95% of the active ingredient. Single-dose forms of administration preferably comprise about 20% to about 90% of the active ingredient and administration forms which are not single-dose preferably comprise about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The cosmetic and/or medical compositions of the present invention are prepared in a manner known per se, for example by means of conventional mixing, granulating, coating, dissolving or lyophilising processes.

Preferably, solutions of the active ingredient, and in addition also suspensions or dispersions, especially isotonic aqueous solutions, dispersions or suspensions, are used, it being possible for these to be prepared before use, for example in the case of lyophilised compositions which comprise the active substance by itself or together with a carrier, for example mannitol. The compositions can be sterilized and/or comprise excipients, for example, preservatives, stabilisers, wetting agents and/or emulsifiers, solubilizing agents, salts for regulating the osmotic pressure and/or buffers, and they are prepared in a manner known per se, for example by means of conventional dissolving or lyophilising processes. The solutions or suspensions mentioned can comprise viscosity-increasing substances, such as sodium carboxymethylcellulose, carboxymethylcellulose, dextran, polyvinylpyrrolidone or gelatine.

Suspensions in oil comprise, as the oily component, vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms (e., lauric acid, tridecylic acid, myristic acid, pentadecylic acid, palmitic acid, margaric acid, stearic acid, acid, arachidonic acid, behenic acid, and the like) or corresponding unsaturated acids (e.g., oleic acid, elaidic acid, euric acid, brasidic acid or linoleic acid). Other additional ingredients known in the art can be included if desired (e.g., antioxidants such as vitamin E, β-carotene, or 3,5-di-tert-butyl-4-hydroxytoluene, and the like). The alcohol component of these fatty acid esters generally contains no more than about 6 carbon atoms and can be mono- or polyhydric. Mono-, di-, or trihydric alcohols such as methanol, ethanol, propanol, butanol, or pentanol, or isomers thereof, can be used; glycols and glycerols are generally preferred. Fatty acid esters can therefore include, for example, ethyl oleate, isopropyl myristate, isopropyl palmitate, "Labrafil M 2375" (polyoxyethylene glycerol trioleate from Gattefoseé, Paris), "Labrafil M 1944 CS" (unsaturated polyglycolated glycerides prepared by an alcoholysis of apricot kernel oil and made up of glycerides and polyethylene glycol esters; from Gattefoseé, Paris), "Labrasol" (saturated polyglycolated glycerides prepared by an alcoholysis of TCM and made up of glycerides and polyethylene glycol esters; from Gattefoseé, Paris), and/or "Miglyol 812" (triglyceride of saturated fatty acids of chain length C8 to C12 from Hüls A G, Germany), and in particular vegetable oils, such as cottonseed oil, almond oil, olive oil, castor oil, sesame oil, soybean oil and, in particular, groundnut oil.

Suitable carriers are, in particular, fillers such as sugars, for example lactose, sucrose, mannitol or sorbitol, cellulose preparations and/or calcium phosphates, preferably calcium phosphate or dicalcium phosphate, and binders such as starches, preferably corn, wheat, rice or potato starch. methylcellulose, hydroxypropylmethylcellulose, sodium carboxymethylcellulose and/or polyvinylpyrrolidine, and/or if desired disintegrants such as the above-mentioned starches and further carboxymethyl starch, crosslinked polyvinylpyrrolidine, alginic acid and its salts, preferably sodium alginate. Other neutral substances are flow regulators and lubricants, preferably salicylic acid, talc, stearic acid and its salts such as magnesium and/or calcium stearate, polyethylene glycol or its derivatives. The cores of the coated tablets may be coated with suitable coatings which may be resistant to gastric juice, the coatings used being, inter alia, concentrated sugar solutions which may contain gum arabic, talc, polyvinylpyrrolidine, polyethylene glycol and/or titanium dioxide, as well as coating solutions in suitable organic solvents or solvent mixtures, or for the preparation of gastric juice-resistant coatings with solutions of suitable cellulose preparations such as acetylcellulose phthalate or hydroxypropylmethylcellulose phthalate. Dyes or pigments are admixed, for example, to identify or characterize different doses of active ingredient.

Other forms of administration are, for example, syrups prepared in a conventional manner which contain the active ingredient, e.g. in suspended form and in a concentration of about 5 to 20%, preferably about 10% or a similar concentration which allows a suitable individual dose, e.g. when 5 or 10 ml. Other forms are, for example, powder or liquid concentrates for the preparation of cocktails, for example in milk. Such concentrates may also be packaged in an amount corresponding to a unit dose.

Ointments are oil-in-water emulsions, which comprise not more than 70%, but preferably 20-50% of water or aqueous phase. The fatty phase consists, in particular, hydrocarbons, for example vaseline, paraffin oil or hard paraffin's, which preferably comprise suitable hydroxy compounds, such as fatty alcohol's or esters thereof, for example cetyl alcohol or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example, glycerol, propylene glycol, sorbitol and/or polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example, hydrogenated coconut-fatty acid triglycerides, or, preferably, hydrogenated oils, for example hydrogenated groundnut or castor oil, and furthermore fatty acid partial esters of glycerol, for example glycerol mono- and/or distearate, and for example, the fatty alcohols. They also can contain emulsifiers and/or additives mentioned in connection with the ointments which increase uptake of water.

Creams are oil-in-water emulsions, which comprise more than 50% of water. Oily bases used are, in particular, fatty alcohols, for example, lauryl, cetyl or stearyl alcohols, fatty acids, for example palmitic or stearic acid, liquid to solid waxes, for example isopropyl myristate, wool wax or beeswax, and/or hydrocarbons, for example vaseline (petrolatum) or paraffin oil. Emulsifiers are surface-active substances with predominantly hydrophilic properties, such as corresponding non-ionic emulsifiers, for example fatty acid esters of polyalcohols or ethyleneoxy adducts thereof, such as polyglyceric acid fatty acid esters or polyethylene sorbitan fatty esters (Tweens), and furthermore polyoxyethylene fatty alcohol ethers or polyoxyethylene fatty acid esters, or corresponding ionic emulsifiers, such as alkali metal salts of fatty alcohol sulphates, for example, sodium lauryl sulphate, sodium cetyl sulphate or sodium stearyl sulphate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and/or polyethylene glycols, and furthermore preservatives and odoriferous substances.

Pastes are creams and ointments having secretion-absorbing powder constituents, such as metal oxides, for example, titanium oxide or zinc oxide, and furthermore talc and/or aluminium silicates, which have the task of binding the moisture or secretions present.

Foams (i.e., liquid oil-in-water emulsions packaged in aerosol form) can be administered from pressurised containers. Propellant gases include halogenated hydrocarbons, such as polyhalogenated alkanes such as dichlorofluoromethane and dichlorotetrafluoroethane, or, preferably, non-halogenated gaseous hydrocarbons, air, $N_2O$, or carbon dioxide. The oily phases used are, inter alia, those mentioned above for ointments and creams, and the additives mentioned there are likewise used.

Tinctures and solutions usually comprise an aqueous-ethanolic base to which, humectants for reducing evaporation, such as polyalcohols (e.g., glycerol, glycols, polyethylene glycol) and re-oiling substances, such as fatty acid esters with lower polyethylene glycols (e.g., lipophilic substances soluble in the aqueous mixture) to substitute the fatty substances removed from the skin with the ethanol, and, if necessary or desired, other excipients and additives, are admixed.

The invention also relates to a process or method for treatment of the disease states mentioned above. The compounds can be administered prophylactically or therapeutically as such or in the form of pharmaceutical or cosmetical compositions, preferably in an amount, which is effective against the diseases mentioned. With a warm-blooded animal, for example, a human requiring such treatment, the compounds are used, in particular, in the form of pharmaceutical composition.

EXAMPLES

The following examples serve to illustrate the invention without limiting the scope thereof. All references cited in the present specification are hereby incorporated by reference Unless otherwise stated, all percentages and the like amounts are based on weight.

Example 1 Preparation of Crystalline Para-Topolin Mesylate p-Topolin, free base (241 mg; 1 mmol) was suspended in stirred methanol (10 ml) at room temperature, and methanesulphonic acid (100 mg; 1.03 mmol) was added. After a short time, the suspension changed into clear yellow solution. The resulting reaction mixture was stirred at room temperature for 15 minutes and then evaporated on rotary vacuum evaporator to yellow solid residue which was treated with acetone (10 ml) to obtain yellowish crystalline powder. The product was filtered off, washed with acetone (3×5 ml) and dried at 60° C. to constant weight.

Yield: 300 mg (88%); purity (HPLC-UV/VIS): 99%+; ESI-MS: [M+H]$^+$=242.2

Yellowish translucent crystals were prepared by the dissolution of the solid substance in methanol to free crystallization by evaporation of the solvent for 7 days.

Example 2: Determination of Melting Point of Crystalline Para-Topolin Mesylate and Comparison with the Melting Point of Para-Topolin Base Melting point of para-topolin mesylate crystalline salt was established at Büchi Melting point B-540 apparatus and compared to para-topolin free base. While the melting point interval for para-topolin crystalline mesylate salt was established to 186-188° C., melting point of original para-topolin base was 281-283° C. It means that melting points of these two compounds differ significantly, the difference is 95° C. Both materials used for the measurement were crystalline white solids.

Example 3 X-Ray Powder Diffraction (XRPD) of Crystalline Para-Topolin Mesylate X-ray powder diffraction studies were performed on a Bruker D8 Advance ECO diffractometer with Cu K-alpha radiation and SSD160 detector. Approximately 5 mg of sample was gently compressed on the XRPD sample holder. The sample was then loaded into a Bruker D8-Discover diffractometer in transmission mode and analyzed using the experimental conditions shown below: XRPD measurement conditions

| Scan axis gonio | |
| --- | --- |
| Start position [°2th.] | 4.0000 |
| End position [°2th.] | 40.00 |
| Step size [°2th.] | 0.0100 |
| Scan step time [s] | 0.3 (48) s |
| Scan type | continuous |
| Divergence slit type | fixed |
| Divergence slit size [°] | 0.3000 |
| Sample length [mm] | 10.00 |
| Receiving slit size [mm] | — |
| Measurement temperature [° C.] | 25.00 |
| Anode material | cu |
| K-alpha1 [å] | 1.54060 |
| K-alpha2 [å] | 1.54443 |
| K-beta [å] | 1.39225 |
| K-a2/k-a1 ratio | 0.50000 |
| Generator settings | 40 ma, 25 kv |
| Goniometer radius [mm] | 250.00 |
| Dist. Focus-diverg. Slit [mm] | 110.00 |
| Ni Kbeta filter | yes |
| Incident beam monochromator | no |
| Spinning | no |

Figure 1:
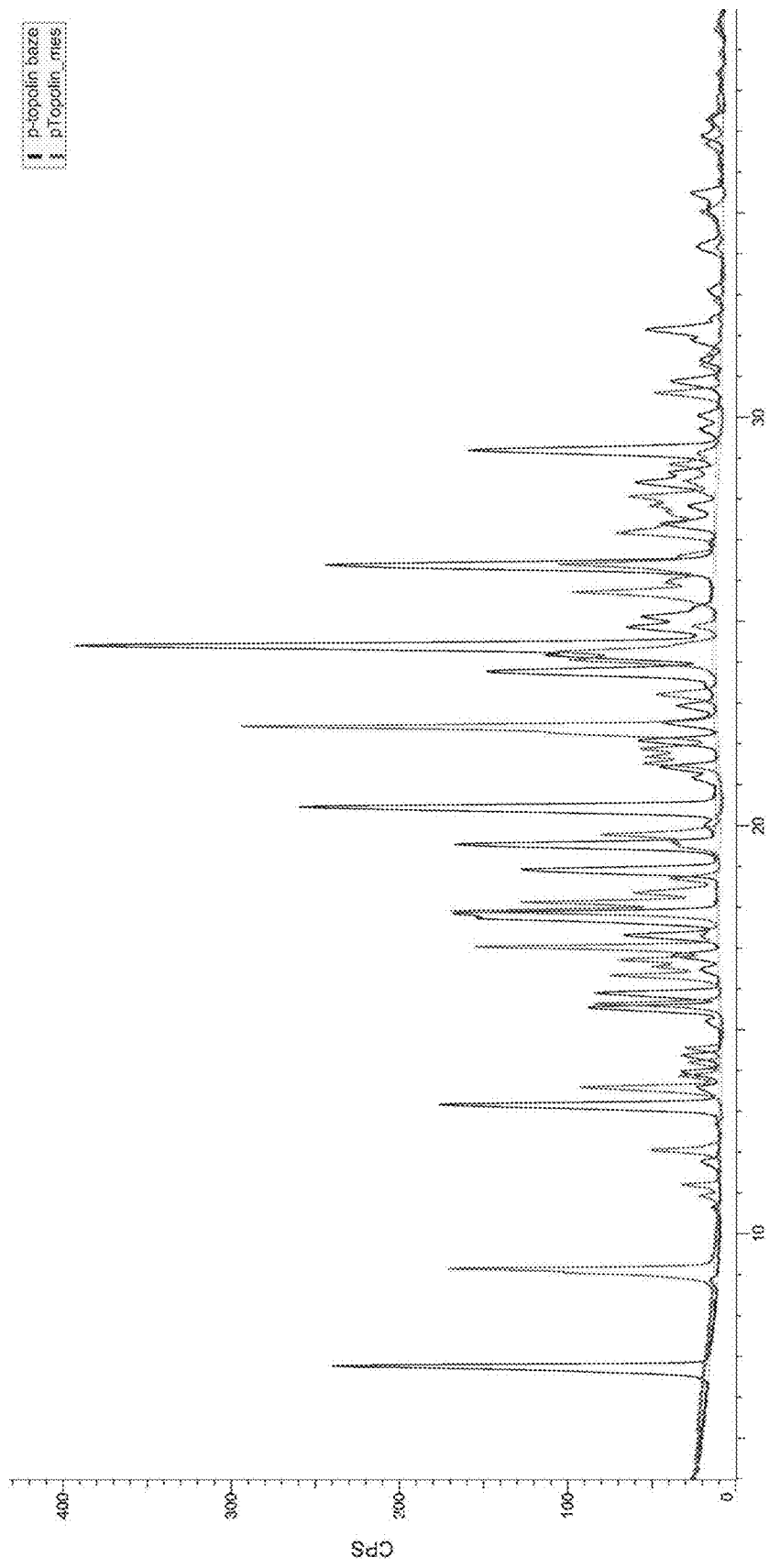
FIG. 1: Comparison of XRPD patterns of para-topolin mesylate crystalline salt (p-topolin mes) and para-topolin (p-topolin base).

The XRPD patterns for para-topolin mesylate crystalline salt as well as for para-topolin were obtained using the procedure described above. FIG. 1 shows a comparison of both these patterns. As apparent, the patterns significantly differ. Para-topolin mesylate crystalline salt is characterized by an X-ray powder diffraction (XRPD) pattern that has the representative peaks given in Table 1. They differ from the peaks that characterize para-topolin which are given in Table 2. Both tables show the relative intensities of the peaks, d-spacing and the respective 2θ angles.

TABLE 1

XRPD angles, d-spacing and relative intensities for para-topolin mesylate

| Position (°2θ) | d-spacing | Rel. Intensity |
| --- | --- | --- |
| 9.049 | 9.76473 | 34.00% |
| 9.146 | 9.66095 | 61.00% |
| 10.924 | 8.09291 | 3.90% |
| 11.189 | 7.90175 | 7.10% |
| 12.047 | 7.3409 | 15.60% |
| 12.67 | 6.98133 | 1.40% |
| 13.569 | 6.52029 | 28.00% |
| 13.858 | 6.38532 | 8.10% |
| 14.188 | 6.23735 | 7.10% |
| 14.538 | 6.08798 | 7.20% |
| 15.629 | 5.66533 | 28.00% |
| 16.329 | 5.42417 | 24.40% |
| 16.572 | 5.34504 | 13.00% |
| 16.698 | 5.30489 | 21.20% |
| 17.021 | 5.2052 | 51.50% |
| 17.318 | 5.11653 | 4.30% |
| 17.424 | 5.08561 | 3.00% |
| 17.904 | 4.95037 | 59.40% |
| 18.11 | 4.89436 | 39.90% |
| 18.361 | 4.82823 | 19.00% |
| 18.706 | 4.73993 | 10.80% |
| 19.583 | 4.52944 | 10.70% |
| 19.779 | 4.485 | 26.50% |
| 20.201 | 4.39237 | 0.90% |
| 21.518 | 4.12628 | 17.40% |
| 21.698 | 4.09245 | 15.40% |
| 21.87 | 4.0608 | 18.10% |
| 22.262 | 3.99002 | 37.00% |
| 22.409 | 3.96422 | 100.00% |
| 23.21 | 3.82922 | 13.70% |
| 24.06 | 3.69581 | 32.80% |
| 24.112 | 3.688 | 27.60% |
| 24.227 | 3.6707 | 32.60% |
| 24.881 | 3.57573 | 5.30% |
| 25.712 | 3.46203 | 30.60% |
| 25.973 | 3.42784 | 11.10% |
| 26.391 | 3.37442 | 34.80% |
| 26.56 | 3.35339 | 7.70% |
| 27.19 | 3.27711 | 20.10% |
| 27.045 | 3.29436 | 7.40% |
| 27.311 | 3.26288 | 12.60% |
| 27.686 | 3.21953 | 11.30% |
| 27.832 | 3.20289 | 16.50% |
| 28.04 | 3.17958 | 18.50% |
| 28.433 | 3.13661 | 6.70% |
| 28.851 | 3.09205 | 11.20% |
| 29.104 | 3.06582 | 5.00% |
| 30.593 | 2.91981 | 15.00% |
| 31.017 | 2.88087 | 1.30% |
| 31.292 | 2.85623 | 4.80% |
| 31.543 | 2.83409 | 2.60% |
| 32.06 | 2.78953 | 0.50% |
| 32.441 | 2.75766 | 0.90% |
| 32.861 | 2.72331 | 1.80% |
| 33.261 | 2.69152 | 0.70% |
| 34.146 | 2.62369 | 1.70% |
| 34.639 | 2.58749 | 1.30% |
| 35.023 | 2.55998 | 4.50% |
| 35.773 | 2.50803 | 1.00% |
| 36.182 | 2.48062 | 1.10% |
| 36.692 | 2.44732 | 4.20% |
| 37.299 | 2.40884 | 3.90% |
| 37.802 | 2.37797 | 1.00% |
| 38.391 | 2.34284 | 1.50% |
| 38.897 | 2.31351 | 0.70% |
| 39.514 | 2.27878 | 1.80% |

TABLE 2

XRPD angles, d-spacing and relative intensities for para-topolin free base

| Position (°2θ) | d spacing | Rel. Intensity |
|---|---|---|
| 6.749 | 13.08594 | 55.80% |
| 8.858 | 9.97457 | 1.00% |
| 10.631 | 8.31467 | 1.00% |
| 11.76 | 7.51896 | 3.00% |
| 13.148 | 6.72814 | 43.30% |
| 13.567 | 6.52143 | 3.30% |
| 13.954 | 6.34164 | 5.70% |
| 14.361 | 6.16281 | 6.00% |
| 15.199 | 5.82456 | 2.10% |
| 15.533 | 5.70029 | 20.60% |
| 15.887 | 5.57406 | 18.60% |
| 16.476 | 5.37596 | 2.90% |
| 16.821 | 5.2665 | 7.10% |
| 17.307 | 5.11956 | 14.40% |
| 17.723 | 5.00039 | 38.20% |
| 17.852 | 4.9646 | 42.30% |
| 18.907 | 4.68984 | 30.40% |
| 19.531 | 4.54138 | 41.10% |
| 20.014 | 4.43284 | 1.60% |
| 20.442 | 4.34101 | 64.70% |
| 21.171 | 4.19322 | 3.50% |
| 21.424 | 4.14415 | 8.80% |
| 22.074 | 4.02358 | 12.10% |
| 22.516 | 3.94557 | 8.20% |
| 22.929 | 3.87556 | 5.80% |
| 23.509 | 3.78124 | 1.30% |
| 23.766 | 3.74081 | 36.20% |
| 24.201 | 3.67456 | 25.70% |
| 24.397 | 3.64555 | 100.00% |
| 24.86 | 3.57867 | 13.70% |
| 25.106 | 3.54423 | 11.00% |
| 25.271 | 3.52137 | 3.30% |
| 26.371 | 3.37702 | 60.60% |
| 26.902 | 3.31153 | 0.60% |
| 27.388 | 3.2538 | 8.20% |
| 27.824 | 3.20383 | 4.30% |
| 28.407 | 3.13936 | 12.80% |
| 28.607 | 3.11784 | 6.90% |
| 29.19 | 3.05695 | 39.80% |
| 29.708 | 3.00484 | 3.00% |
| 30.035 | 2.97278 | 3.20% |
| 30.88 | 2.89333 | 7.50% |
| 31.412 | 2.84558 | 3.30% |
| 31.918 | 2.8016 | 4.50% |
| 32.143 | 2.78253 | 11.80% |
| 32.396 | 2.76136 | 1.60% |
| 33.1 | 2.7042 | 2.20% |
| 34.177 | 2.62143 | 4.20% |
| 35.093 | 2.55506 | 2.20% |
| 35.474 | 2.52849 | 4.90% |
| 36.368 | 2.46834 | 0.60% |
| 36.889 | 2.43471 | 3.20% |
| 37.273 | 2.41045 | 1.90% |
| 38.063 | 2.36222 | 0.70% |
| 38.42 | 2.34111 | 0.70% |
| 39.532 | 2.2778 | 0.50% |
| 39.686 | 2.26928 | 0.60% |

Example 4: $^1$H Nuclear Magnetic Resonance (NMR) of Para-Topolin Mesylate, and Comparison with $^1$H NMR Spectra of Para-Topolin $^1$H NMR was performed on a JEOL 500 SS operating at the temperature of 300 K and a frequency of 500.13 MHz. The samples were prepared by dissolving the compounds in DMSO-d6. Tetramethylsilane (TMS) was used as an internal standard. Calibration of chemical shift related to shift of residual solvent peak in $^1$H DMSO-$d_6$, 2.50 ppm. Each sample was prepared in ca. 5 mg/ml concentration.

Chemical shifts identified in the spectra of 6-(4-hydroxybenzylamino) purinium mesylate (para-topolin mesylate) crystalline salt respond to described chemical compound and are as follows: $^1$H NMR (500 MHz, DMSO-d6) δ 9.48 (s, 1H), 8.66 (s, 1H), 8.51 (s, 1H), 7.22 (d, J=8.5 Hz, 2H), 6.75 (d, J=8.3 Hz, 2H), 4.70 (d, J=4.6 Hz, 2H), 2.34 (s, 3H); chemical shifts identified in the spectra of 6-(4-hydroxybenzylamino) purine (para-topolin) are as follows: $^1$H NMR (500 MHZ, DMSO-d6) δ 12.89 (s, 1H), 9.23 (s, 1H), 8.17 (s, 1H), 8.09 (s, 2H), 7.15 (d, J=8.4 Hz, 2H), 6.66 (d, J=8.3 Hz, 2H), 4.57 (s, 2H). When chemical shifts of both compounds are compared, significant differences can be found, especially of those chemical shifts that are in the vicinity of the protonated hydrogen in 6-(4-hydroxybenzylamino) purinium as compared to 6-(4-hydroxybenzylamino) purine base.

Example 5: Aqueous Solubility of Para-Topolin Mesylate

Aqueous solubility was measured using the following protocol. Supersaturated solution of para-topolin mesylate salt in water was prepared. The solution was filtrated from visible undissolved particles of the salt to obtain saturated solution. Saturated solution was diluted 1:10 000 and measured using HPLC Alliance Waters 2690 with C18 Symmetry column with the diameter 2.1 mm and 150 mm length with a porosity of 5 μm. The sample was dissolved in the mobile phase (MeOH:HCOONH$_4$-1:9). The sample was washed with a methanol gradient (10-90%, 35 min) at pH 4 and a flow rate of 0.3 ml/min. The absorbances of the components were detected in the UV region at 210-400 nm. The peak area was 2729231. The standard was measured as shown in the Table 3 below. Obtained peak area was compared to area peaks measured at certain concentration and the final concentration of saturated solution was determined.

TABLE 3

Peak areas for various concentrations of para-topolin crystalline salt in water.

| c (μM) | peak area |
|---|---|
| 50 | 1101534 |
| 100 | 2091000 |
| 250 | 5578605 |

It means that the concentration of para-topolin mesylate crystalline salt water is approximately 1.208 M, i.e. 407 mg/ml, which is several orders of magnitude more when compared to para-topolin free base. Para-topolin base is reported to exhibit an aqueous solubility <0.04 mg/ml.

Example 6: Solubility of Para-Topolin Mesylate and Para-Topolin Base in Various Organic Solvents Solubility in various organic solvents was measured using the following protocol. Approximately 10 mg portions of para-topolin and crystalline para-topolin mesylate salt were placed in different vials, separately. Five volume aliquots of each solvent were added exclusively to a vial. Between each addition, the mixture was checked for dissolution and if no dissolution was apparent, the procedure was continued until dissolution was observed or further volumes had been added. The results are shown in Table 4.

TABLE 4

Solubility of p-topolin and p-topolin mesylate in various solvents

| Solvent | p-topolin | p-topolin mesylate |
|---|---|---|
| methanol | 0.25 mg/ml | 5 mg/ml |
| ethanol | 0.25 mg/ml | 0.4 mg/ml |
| DMF | 5 mg/ml | 14 mg/ml |
| DMSO | 6.66 mg/ml | 10 mg/ml |
| acetone | 0.2 mg/ml | 0.33 mg/ml |
| heptane | <0.1 mg/ml | <0.1 mg/ml |
| acetonitrile | <0.25 mg/ml | <0.25 mg/ml |

Figure 2:
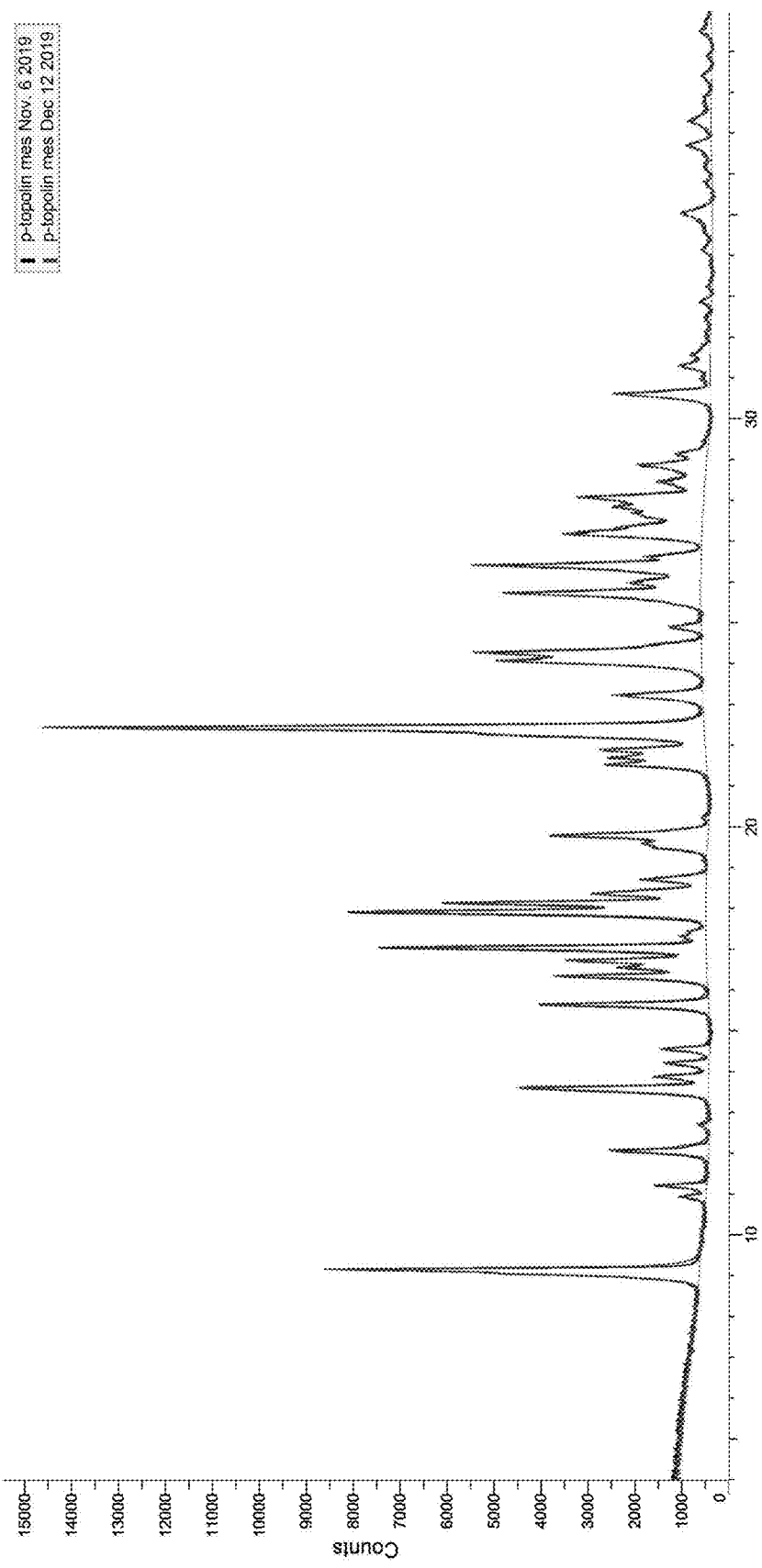
FIG. 2: depicts the results of stability XRPD study of para-topolin mesylate crystalline salt measured after 30 days of storage at the temperature of 25° C.—no structural pattern changes detected.

Example 7: Stability Study of Crystalline Para-Topolin Mesylate Salt by XRPD Diffraction Sample stability was tested at at 25° C. for 14 days on light. No structure nor color change were observed after 30 days. XRPD of samples were taken after 30 days to investigate any solid form change (any difractogram/pattern change). FIG. 2 shows the XRPD patterns of the initial sample and sample of crystalline para-topolin mesylate salt after 30 days at 25° C.

Example 8: Disproportionation Study of Crystalline Para-Topolin Mesylate Salt

A 50 mg sample of crystalline para-topolin mesylate salt was dissolved in 1 ml of distilled water, kept in solution for ca. 48 hours and then crystallized and checked by XRPD for disproportionation. No signs of disproportionation were observed.

Example 9: Single Crystal X-Ray Diffraction of Crystalline Para-Topolin Mesylate and Description of its Molecular and Crystal Structure Single crystal preparation: Crystals were grown from solutions of crystalline para-topolin mesylate salt (ca. 100 mg) dissolved in methanol (30 cm$^3$). The solution was then allowed to slowly evaporate through pierced parafilm. Translucent crystals were apparent after ca. 1 week of evaporation.

Single crystal X-ray diffraction: A long shaped crystals of the sample were selected for data collection. Diffraction data were collected using four/circle diffractometer Supernova with mirror-collimated Cu/Kα radiation from a micro-focus sealed X-ray tube, equipped with the CCD areal detector Atlas S2 operation at 105 K.

Figure 3:
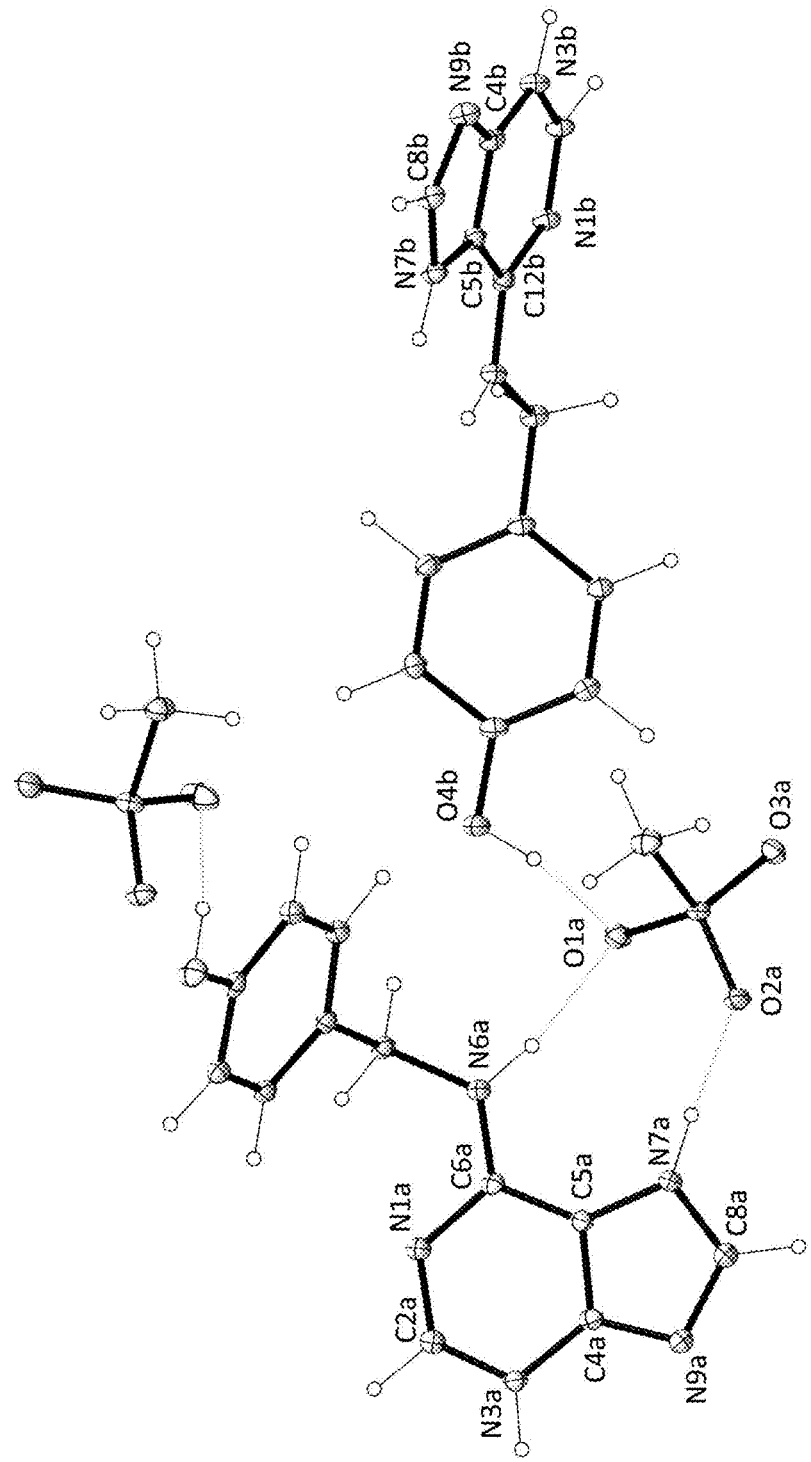
FIG. 3: shows the structure of centrosymmetric dimer of para-topolin mesylate crystalline salt including intermolecular hydrogen bond network.
Figure 4:
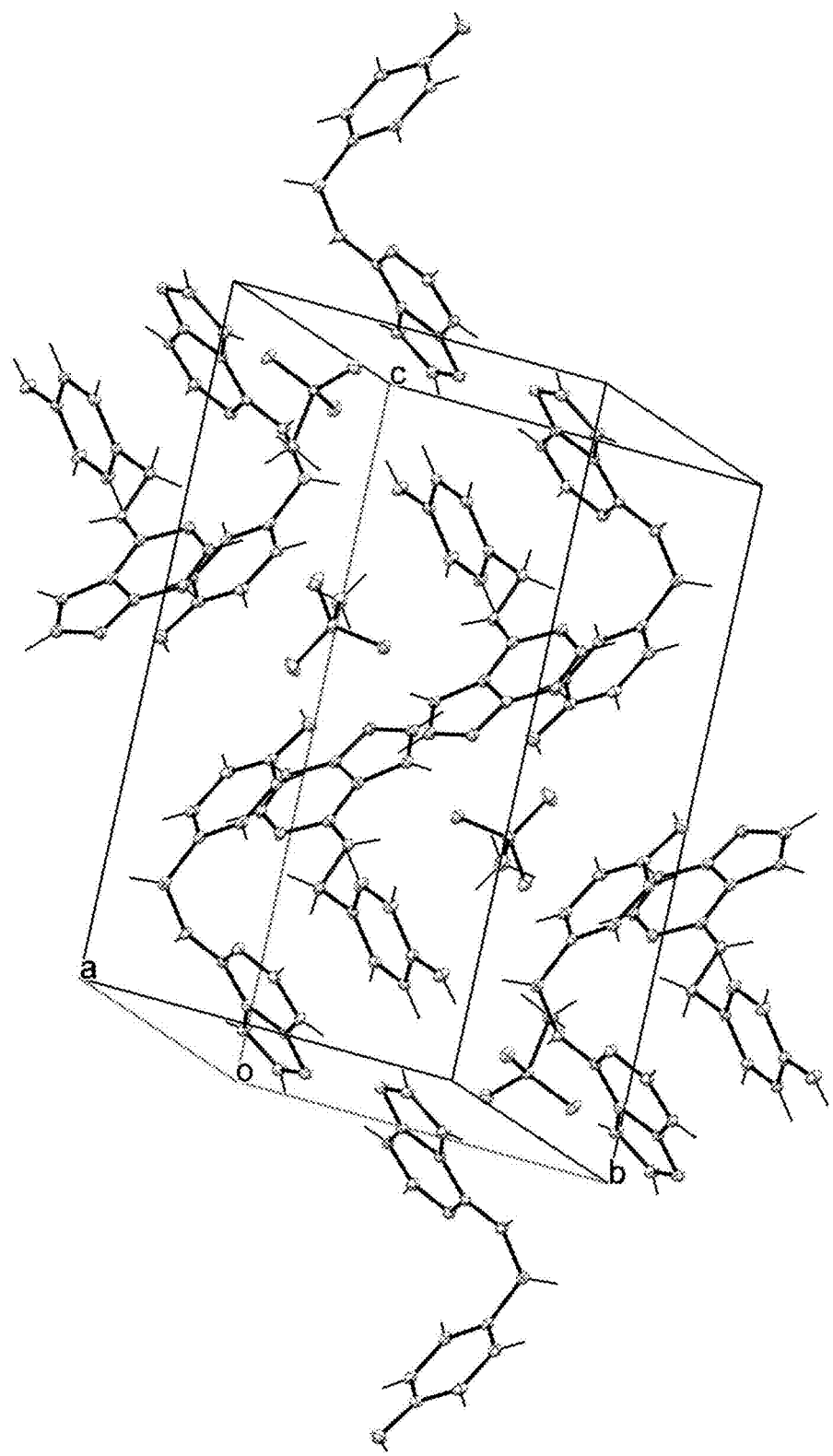
FIG. 4: shows crystal structure (crystal packing) of para-topolin mesylate crystalline salt including intermolecular hydrogen bond network.

On indexing the data set, the crystal structure was determined to be a centrosymetric dimer. Crystal system was identified as triclinic with P-1 space group and with the following cell dimensions: a=7.5356, b=10.5681, c=19.7793 Å, α=101.1060°, β=95.940°, γ=105.3230° and cell volume V=1470.75 Å$^3$. The structure model was found using Superflip or SHELXT and refined by full-matrix least-squares by JANA2006 software. Data collection, redaction and absorption corrections for all compounds were carried out using CrysAlisPro Software (Rigaku, Oxford Diffraction, 2018, CrysAlis version 1.171.40.35a). The asymmetric unit of the title compound is formed by a 6-(4-hydroxybenzylamino)purinium (para-topolin) cation and a mesylate (methylsulphonate) anion. Cation is protonized at one of the nitrogen atom of purine moiety and the compound crystallizes in triclinic crystal system with P-1 spatial group. Hydrogen atoms attached to carbon were placed in calculated positions. Some hydrogen atoms attached to oxygen could be located in difference maps. Intermolecular hydrogen bonds between N—H atom of purine and oxygen atom of mesylate anion connect two molecules as centrosymetric dimers. These hydrogen bonds stabilize the system and connect N6a . . . H6a of purine structure with O1a of mesylate anion, N7a . . . H7a of purine structure with O2a of mesylate anion, O4b . . . H1o4b of hydroxyl attached to benzyle ring of para-topolin molecule with O1a of mesylate anion and vice versa O4b . . . H4b of para topolin molecule with O1b of mesylate (FIG. 3). Besides, purine based cations are linked by two hydrogen bonds between N3a-H3a . . . N$_9$a of the further topoline molecule in crystal packing (FIG. 4).

The final 'conventional' R-factor [based on F and 6049 reflections with [F$^2$>2σ(F$^2$)] was 0.0271. The single crystal structure of crystalline para-topolin mesylate salt shows that the compound has general formula of $C_{13}H_{15}N_5O_4S$ with para-topolin cation and mesylate anion. Centrosymetric dimers of asymmetric unit are bond together by a number of above listed intermolecular hydrogen bonds that are mainly realized between protonized cation and mesylate anion that contributes to excellent solubility of the compound in water. Hydrogen atom placement using X-ray data is usually regarded as tentative, but the position of particular molecules within the frame of the structure is persuading. Besides, important torsion angles, that also have impact on physical properties and solubility of the compounds are strongly influenced by the formation of such thick network of intermolecular hydrogen bonding.

Example 10: Ability to Scavenge Free Radicals, Determined by ORAC

The ability of the substance to scavenge free radicals in vitro was determined using the ORAC (Oxygen Radical Absorbance Capacity) method. Briefly, 100 μl of fluorescein (500 mM) and 25 μl of tested substance solution were pipetted into each well of a 96-well microtiter plate preheated to 37° C. The reaction itself was started by the addition of 25 μL 250 mM AAPH. After shaking for 5 s, the fluorescence (Ex. 485 nm, Em. 510 nm) was read every 3 min for 90 min using an Infinite 200 instrument (TECAN, Switzerland). The area under the curve was used to express the antioxidant capacity relative to trolox, which is used as a standard. Substances with ORAC activity higher than 1 are more effective than trolox, which is the hydrophilic equivalent of vitamin E. Trolox, a water-soluble analogue of vitamin E, is known for its antioxidant activity, which has also been shown to be responsible for its protective activity in human cells. The ORAC test, which is generally used to determine antioxidant activity, showed that several cytokinins, such as ortho-topolin (oT), meta-topolin (mT) and para-topolin (pT), were associated with high total antioxidant activity expressed in equivalents of Trolox (TE). Such activities are likely to be closely related to the electron-rich C6-hydroxybenzylamino substituent system. The mesylate salt of para-topolin has been shown to be the most effective substance.

TABLE 5

ORAC data expressed in Trolox equivalents (TE) on equimolar basis

|  | Average(TE) | SD (n = 3) |
|---|---|---|
| 6-(3-hydroxybenzylamino)purine (mT) | 4.509 | 0.687 |
| 6-(2-hydroxybenzylamino)purine (oT) | 7.026 | 1.179 |

TABLE 5-continued

ORAC data expressed in Trolox equivalents (TE) on equimolar basis

|  | Average(TE) | SD (n = 3) |
|---|---|---|
| 6-(4-hydroxybenzylamino)purine (pT) | 16.799 | 0.829 |
| 6-(4-hydroxybenzylamino)purinium mesylate (pT mesylate) | 21.436 | 1.306 |

Example 11: Anti-Inflammatory Activity of Para-Topolin and Para-Topolin Mesylate The anti-inflammatory activity of para-topolin and para-topolin mesylate was determined; cytokinin kinetin was also evaluated as a control. Rat glioma C6 cells (ATCC No. CCL107) were cultured in a monolayer in chemically defined beser medium containing Ham's F10/minimal essential medium (1:1 v/v), 2 mM L-glutamine, 1% (v/v). Minimum vitamins of essential medium (100×), 1% (v/v) minimum essential amino acids (100×), 100 U/ml penicillin, 100 mg/ml streptomycin and 30 nM sodium selenite. Incubation was performed at 37° C. in a 100% humidified atmosphere. The assays were performed in logarithmic growth phase at a density of $2.5 \times 10^5$ cells/cm$^2$. Intracellular cAMP synthesis was induced by the addition of 5 mM (−)-isoproterenol; at the same time, various concentrations of tested compounds were added at the same time as (−)-isoproterenol. After 30 minutes of incubation, the cellular amount of CAMP was determined by ELISA (cAMP-enzyme immunoassay from Amersham). $IC_{50}$ values were determined from the two-dose dose-response curve. The following results were obtained:

|  | Anti-inflammatory activity $IC_{50}$ (µM) |
|---|---|
| 6-furfurylaminopurine (kinetin) | 0 |
| 6-(4-hydroxybenzylamino)purine (para-topolin, pT) | 7 |
| 6-(4-hydroxybenzylamino)purin mesylate (para-topolin mesylate, pTmes) | 13 |

Para-topolin and para-topolin mesylate showed anti-inflammatory activity, while the mesylate was twice more active than the initial free base para-topolin. Kinetin was inactive in tested protocol and was used as cytokinin control.

Example 12: Effect of pT Mesylate on Senescent Human Diploid Fibroblasts

Senescent human diploid fibroblasts (cells of different levels of passage: passage 20-P20; passage 40—labeled P40; passage 80—labeled P80) were seeded in a 24-well plate (10,000 cells/well). The culture medium (DMEM containing 5 g/l glucose, 2 mM glutamine, 100 U/ml penicillin, 100 µg/ml streptomycin and 10% fetal calf serum) was removed and replaced with culture medium containing test compound in a concentration range of 0 to 12.5 µM. Each concentration was tested in triplicate. The cells were then incubated at 37° C. (without CO 2) for 16 hours in 2 to 3 ml of a solution containing potassium ferricyanide (5 mM), potassium ferrocyanide (5 mM), MgCl 2 (2 mM), X-gal (5-bromo)-4-chloro-3-indolyl-β-D-galactopyranoside (1 mg/ml), in citrate/phosphate buffer, pH 6.0) After this incubation period, cell samples were observed for the presence of blue cells. indicating that X-gal was cleaved (positively senescent cells). In this experiment, senescent cells, but not other cells, were stained blue due to β-galactosidase on the substrate. As shown in Table 6, the color darkened with increasing number of passages. In the oldest cells, there were only blue cells, from bright blue to almost opaque in color. Both para-topolins (base and mesylate salt) were effective in maintaining much lower levels of senescent cells after 80 passages. In the case of long-term culture, the treated cells were able to live 30% longer than the control cells.

TABLE 6

The effect of new compound para-topolin mesylate on the number of senescent cells in human fibroblast culture

| compound | Senescent cells (%) | | |
|---|---|---|---|
| Cell passages | P20 | P40 | P80 |
| control | 3 | 14 | 38 |
| 6-(4-hydroxybenzylamino)purine (para-topolin) | 4 | 14 | 25 |
| 6-(4-hydroxybenzylamino)purine mesylate (para-topolin mesylate) | 3 | 12 | 21 |

Example 13: In Vitro Cytotoxic Activity (Metabolisation of Calcein AM)

Because toxic compounds negatively influence metabolic processes of cells, many standard cytotoxicity assays are based on measurement of metabolisation rate of various artificial substrates. Resulting product is then quantified, for example, by means of spectrometry. The assays can be easily modified for use in 96-well plates. For evaluation of cytotoxicity of the dihydrozeatin derivatives of this invention, a microtiter assay based on quantification of metabolisation of Calcein AM was used. The assay is widely used in drug screening programs and in chemosensitivity testing. In live cells, Calcein AM is enzymatically hydrolysed and accumulation of the resulting calcein is manifested by green fluorescence.

The following cell lines-RPMI 8226 (multiple myeloma), CEM (T-lymphoblastic leukaemia), K562 (chronic myelogenous leukaemia), HL-60 (promyelocytic leukaemia), MCF-7 (breast adenocarcinoma), HeLa (cervical carcinoma), G361 (malignant melanoma), HOS (human osteosarcoma) and BJ (human foreskin fibroblasts)-were obtained from the American Type Culture Collection (Manassas, VA, USA). These cells were maintained in standard DMEM or RPMI medium (Sigma, MO, USA) supplemented with heat-inactivated fetal bovine serum (10%) 2 mM L-glutamine and penicillin-streptomycin (1%) under standard cell culture conditions (37° C., 5% $CO_2$ in a humid environment) and sub-cultured two or three times per week using the standard trypsinization procedure.

Approximately 10,000 cells in 80 µL of medium were seeded into 96-well microtitre plates. After 12 h incubation, compounds to be tested were added in 20 µl portions. Control cultures were treated with DMSO alone. The final concentration of DMSO in the medium did not exceed 0.5%. Serial, triplicate 3-fold dilutions (six in total, highest concentration in incubations 166 µM) of each compound were tested. After 72 h incubation, Calcein AM solution (Molecular Probes) was added to a final concentration of 1 µg/ml, and the cells were incubated for a further hour. The fluorescence of free calcein was then quantified using a Fluoroscan Ascent fluorometer (Microsystems), and the percentage of surviving cells in each well was calculated by dividing the OD obtained from each cell with exposed cells by the mean OD obtained from control wells×100%. Finally, $IC_{50}$ values (the concentrations causing a 50% decrease in cellular esterase activity) were calculated for each compound from the generated dose-response curves (Kryštof et al., 2005, Bioorg. Med. Chem. Lett. 12, 3283-3286). The $IC_{50}$ values presented here are averages obtained from at least three independent experiments, where individual replicate values fell within 20% of the average. Growth inhibition was estimated using the following equitation: $IC_{50}$= (mean $FD_{drug\ exposed\ wells}$-mean $FD_{blank}$)/(mean $FD_{control\ wells}$-mean $FD_{blank}$)×100%. The $IC_{50}$ value, the drug concentration causing 50% reduction of Calcein AM conversion, was calculated from the obtained dose response curves.

Cytoxicity of compounds was tested on panel of cell lines of different histogenetic and species origin. As shown in Table 7, $IC_{50}$ of para-topolin base and para-topolin mesylate exceeded maximal concentration tested which suggests that the compounds could be applied at concentrations causing desired effect without negative side effects.

TABLE 7

Cytotoxic activity of para-topolin mesylate and para-topolin expressed as $IC_{50}$ values in a 3-day Calcein-AM assay. Presented values are averages of at least 3 independent experiments, where individual replicates fall into 20% interval around the average.

| | CEM | HL60 | K562 | RPMI 8226 | HOS | MCF7 | G361 | HELA |
|---|---|---|---|---|---|---|---|---|
| para-topolin | >167 | >167 | 140 | >167 | >167 | >167 | >167 | >167 |
| para-topolin mesylate salt | >167 | >167 | >167 | >167 | >167 | >167 | >167 | >167 |

Example 14: In Vitro Cytotoxic Activity in Normal Fibroblasts (Metabolisation of MTT)

MTT (metabolic tetrazolium toxicity) assay is a standard colorimetric assay for evaluation of cytotoxicity. Mitochondrial dehydrogenase activity converts yellow MTT into violet formazan which is measured by means of spectrometry. Human diploid fibroblast BJ (passage 18-22) were seeded into 96-well plate (5.000 cells per well). After 6 hours cultivation medium (DMEM with 5 g/l glucose, 2 mM glutamine, 100 U/ml penicillin, 100 mmg/ml streptomycin, 10% fetal calf serum and sodium bicarbonate) was replaced with the cultivation medium containing test compounds in concentration range of 0-200 µM. Highest concentration was adjusted if the solubility of the compound was limiting. Every concentration was tested in pentaplicate. MTT was added to the cells after 72 hours incubation (final concentration 0.5 mg/ml) and incubation continued for another 3 hours. MTT was solubilised by DMSO and absorbance at 570 nm was measured. Growth inhibition (GI) was estimated using the following equitation: GI=(mean A drug exposed wells-mean $A_{blank}$/mean $A_{control\ wells}$-mean $A_{blank}$)×100%. The $GI_{20}$ value, the drug concentration causing 20% decrease in mitochondrial dehydrogenase activity, was calculated from the obtained dose response curves. As shown in Table 8, $GI_{20}$ of para-topolin mesylate exceeded maximal concentration tested which suggests that the compounds could be applied at concentrations causing desired effect without negative side effects. On the other hand, many other natural isoprenoid cytokinin bases and ribosides exhibited high cytotoxicity.

TABLE 8

Cytotoxicity for Human Diploid Fibroblasts ($GI_{20}$, µM)

| Compound | BJ |
|---|---|
| 6-(4-hydroxybenzylamino)purine (para-topolin) | 138 |
| 6-(4-hydroxybenzylamino)purine mesylate (para-topolin mesylate) | >167 |
| 6-(benzylamino)purine riboside | 1.7 |
| 6-furfurylaminopurine | >167 |
| 6-furfurylaminopurine riboside | 2.1 |

Example 15: Ames Test

Para-topolin and para-topolin mesylate were tested for mutagenicity by a bacterial reverse mutation assay. The performance of the test was based on the EU method B.13/14 Mutagenicity-Reverse mutation test using bacteria, Council Regulation (EC) No. 440/2008, which is analogous to the OECD Test Guideline No. 471. Four indicators of *Salmonella typhimurium* strain TA 98, TA 100, TA 1535, TA 1537 were used and one *Escherichia coli* strain WP2 avrA was also used. The test substances were dissolved in dimethyl sulfoxide (DMSO) and tested at doses of 10-1000 µg per plate, which was applied to 0.1 ml plates. The experiments were performed with metabolic activation with rat liver supernatant and cofactor mixture as well as without metabolic activation. When tested in the above arrangement, the test substances proved to be non-mutagenic for all test strains used with metabolic activation as well as without metabolic activation.

Example 16: Bioavailability of Para-Topolin Base and of Para-Topolin Mesylate Salt, Upon Intraduodenal and Intravenous Administration in Male Sprague-Dawley Rats Preparation of Dosing Solutions for In-Vivo Study: Para-topolin and para-topolin mesylate salt were stored at room temperature under desiccant and protected from light. The dosing solutions were prepared fresh from powders on the day of dosing. The dosing solution for intravenous administration (IV) was prepared at 1 mg/mL (free acid) in 50:50 DMSO: saline. The dosing solution for intraduodenal administration (ID) was prepared at 2 mg/mL in a 0.2% sodium carboxymethyl cellulose (Na CMC) aqueous solution.

Administration to Animals: The pharmacokinetics of para-topolin base and mesylate was evaluated in fasted male Sprague-Dawley rats. Each animal was fitted with a jugular vein cannula (JVC) for blood sampling. Animals intended for intravenous dosing were fitted with an additional JVC for dose administration. Animals intended for intraduodenal dosing were fitted with an intraduodenal cannula (IDC) for dose administration. Surgically modified animals were housed one per cage. All animals were supplied with a commercial rodent diet (LabDiet, Certified Rodent Diet #5002) ad libitum prior to study initiation. Food was then withheld from the animals for a minimum of twelve hours before the study and during the study, until eight hours post dose when food was provided again. Water was supplied ad libitum. Intraduodenal dosing solutions were administered as a single bolus dose at time zero on the day of dosing. Intravenous doses were administered as a slow IV injection over approximately 1 minute. Blood sampling times began at the end of the infusion. Blood samples were collected. The study design is shown in Table 9.

TABLE 9

Comparative pharmacokinetic study of para-topolin and para-topolin mesylate salt, in rats

| Treatment-Group | Tested Compound | Administration | Dose (ml/kg) | Solution conc. (ml/kg) | Dosed Volume (ml/kg) | Vehicle | Blood Sampling Times |
|---|---|---|---|---|---|---|---|
| 1. | para-topolin | ID | 20 | 10 | 2 | 0.2% NaCMC in H$_2$O | 0, 15, 30 min, 1, 2, 3, 4, 6, 8, 24 h |
| 2. | para-topolin mesylate | ID | 20 | 10 | 2 | 0.2% NaCMC in H$_2$O | 0, 15, 30 min, 1, 2, 3, 4, 6, 8, 24 h |
| 3. | para-topolin | IV | 1 | 1 | 1 | 50% DMSO in saline | 0, 5, 15, 30 min, 1, 2, 3, 4, 6, 8, 24 h |
| 4. | para-topolin mesylate | IV | 1 | 1 | 1 | 50% DMSO saline | 0, 5, 15, 30 min, 1, 2, 3, 4, 6, 8, 24 h |

Each blood sample was collected from the rats via a jugular vein cannula and placed into chilled polypropylene tubes containing sodium heparin as an anticoagulant. Samples were centrifuged at a temperature of 4° C. and at a speed of 13,000 rpm for 5 minutes. Samples were maintained chilled throughout processing. Each plasma sample was split into two aliquots. The first aliquot contained 50 μL of plasma. All remaining plasma volume was used for the second aliquot. Samples were then placed on dry ice, and stored in a freezer set to maintain −60° C. to −80° C. The total concentration of para-topolin in plasma samples were analyzed by LC-MS/MS after an overnight incubation with glucuronidase/arylsulfatase enzyme mixture. Pharmacokinetic parameters were calculated using the WinNonlin software.

Analysis of Plasma Samples: An LC-MS/MS analytical method for the determination of genistein in rat plasma was developed (Novák et al., Phytochemistry, 69, 2008:2214-2224). Prior to sample analysis, a standard curve was analyzed to determine the specificity, range, and linearity of the method. Total para-topolin in plasma samples was determined by pre-treating all samples with β-glucuronidase/arylsulfatase enzymes and incubating prior to analysis. Incubation with the enzyme mix deconjugated any glucuronide or sulfate metabolites of para-topolin back to the parent form.

Acceptance criteria for LC-MS/MS analysis: One standard curve was dispersed throughout each analytical run. At least ⅝ of the standards must be accurate to within ±20%, except at the LLOQ where ±25% is acceptable, in order for the run to pass.

Pharmacokinetic Analysis: Individual plasma concentrations versus time data for para-topolin were subjected to non-compartmental analysis using the pharmacokinetic program WinNonlin v. 4.1. Plasma concentrations below the limit of quantitation (10 ng/mL) were assigned a value of zero for PK analysis only.

Results: The mean plasma concentration and PK profiles of para-topolin compared with para-topolin mesylate salt was markedly different upon ID dosing. The mean peak plasma concentration ($C_{max}$) in case of para-topolin mesylate salt was 4.2-fold higher compared to the peak plasma concentration in case of para-topolin base, 6526±897 ng/mL and 1312±765 ng/mL, respectively. Already within 15 minutes after ID dosing of para-topolin mesylate salt maximum plasma concentration ($C_{max}$) was observed, while the $C_{max}$ of para-topolin base was observed at 2 hours post dose (Table 7). The para-topolin bioavailability from crystalline para-topolin mesylate salt was 53±12% compared to 13±4.1% for para-topolin base (Table 10).

TABLE 10

Pharmacokinetic parameters after intraduodenal administration of 20 mg/kg of respective form (mean ± SD, n = 3).

| PK parameter | para-topolin | para-topolin mesylate |
|---|---|---|
| $C_{max}$ (ng/ml) | 1312 ± 765 | 6526 ± 897 |
| $t_{max}$ (h) | 2.1 ± 0 | 0.82 ± 0.9 |
| $AUC_{last}$ (h · kg · ng/ml/mg) | 408 ± 111 | 1157 ± 342 |
| Bioavailability (%) | 13 ± 4.1 | 53 ± 12 |

Example 17: Formulations

The growth regulatory formulations usually contain from 0.1 to 99% by weight, especially from 0.1 to 95% by weight, of active ingredient mixture comprising a para-topolin mesylate salt of this invention, from 1 to 99.9% by weight of a solid or liquid formulation adjuvant, and from 0 to 25% by weight, especially from 0.1 to 25% by weight, of a surfactant. Whereas commercial products are usually formulated as concentrates, the end user will normally employ dilute formulations. The compositions may also comprise further ingredients, such as stabilizers, e.g., vegetable oils or epoxidised vegetable oils (epoxidised coconut, rapeseed oil or soybean oil), antifoams, e.g., silicone oil, preservatives, viscosity regulators, binders, tackifiers, and also fertilisers or other active ingredients. Preferred formulations have especially the following compositions: (%=percent by weight):

|  | a) | b) | c) | d) |
|---|---|---|---|---|
| Emulsifiable concentrates |  |  |  |  |
| active ingredient | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol ethylene oxide) | — | 2% | — | 2% |
| cyclohexanone | — | — | 10% | 20% |
| aromatic hydrocarbon mixture C9-C12 | 83% | 82% | 53% | 18% |

Emulsions of any desired final concentration can be obtained from such concentrates by dilution with water.

| Solutions |  |  |  |  |
|---|---|---|---|---|
| active ingredient | 5% | 10% | 50% | 90% |
| 1-methoxy-3-( 3-methoxy-propoxy)-propane | — | 20% | 20% | — |
| polyethylene glycol MW 400 | 20% | 10% | — | — |
| octylphenol polyglycol ether (7-8 mol ethylene oxide) | — | — | 30% | 10% |
| aromatic hydrocarbon mixture | 75% | 60% | — | — |

The solutions are suitable for use in the form of microdrops.

| Wettable powders |  |  |  |  |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalenesulfonate | — | 6% | 5% | 6% |
| octylphenol polyglycol ether (7-8 mol ethylene oxide) | — | 1% | 2% | — |

-continued

|                                      | a)   | b)   | c)   | d)   |
|--------------------------------------|------|------|------|------|
| highly dispersed silicic acid        | 1%   | 3%   | 5%   | 10%  |
| kaolin                               | 87%  | 61%  | 37%  | —    |

The active ingredient is mixed thoroughly with the adjuvants and the mixture is thoroughly ground in a suitable mill, affording wettable powders which can be diluted with water to give suspensions of any desired concentration.

Suspension concentrate

|                                      | a)   | b)   | c)   | d)   |
|--------------------------------------|------|------|------|------|
| active ingredient                    | 3%   | 10%  | 25%  | 50%  |
| ethylene glycol                      | 5%   | 5%   | 5%   | 5%   |
| nonylphenol polyglycol ether (15 mol ethylene oxide) | —    | 1%   | 2%   | —    |
| sodium lignosulfonate                | 3%   | 3%   | 4%   | 5%   |
| carboxymethylcellulose               | 1%   | 1%   | 1%   | 1%   |
| 37% aqueous formaldehyde             | 0.2% | 0.2% | 0.2% | 0.2% |
| silicone oil emulsion                | 0.8% | 0.8% | 0.8% | 0.8% |
| water                                | 85%  | 78%  | 64%  | 38%  |

The finely ground active ingredient is intimately mixed with the adjutants, giving a suspension concentrate from which suspensions of any desired concentration can be obtained by dilution with water.

Dry Capsules 5000 capsules, each of them containing 0.25 g para-topolin mesylate, are prepared as follows: Composition: 1250 g active ingredient, 180 g talc, 120 g wheat starch, 80 g magnesium stearate, 20 g lactose.

Preparation process: Finely ground components are pressed through a 0.6 mm mesh. 0.33 g of the mixture is filled in a gelatine capsules by a capsule-filling machine.

Soft Capsules 5000 soft gelatine capsules, each of which contains 0.05 g of one of the para-topolin mesylate salt as active ingredient, are prepared as follows: Composition: 250 g Active ingredient+2 litres Lauroglycol Preparation process: The powdered active ingredient is suspended in Lauroglykol® (propylene glycol laurate, Gattefossé S. A., Saint Priest, France) and ground in a wet-pulveriser to a particle size of about 1 to 3 mm. Portions of in each case 0.419 g of the mixture are then transferred to soft gelatine capsules by means of a capsule-filling machine.

Soft Capsules 5000 soft gelatine capsules, each of which contains 0.05 g of one of the dihydrozeatin derivative as active ingredient, are prepared as follows:

Composition: 250 g Active ingredient+1 litre PEG 400+1 litre Tween 80

Preparation process: The powdered active ingredient is suspended in PEG 400 (polyethylene glycol of Mr between 380 and about 420, Sigma, Fluka, Aldrich, USA) and Tween® 80 (polyoxyethylene sorbitan monolaurate, Atlas Chem. Inc., Inc., USA, supplied by Sigma, Fluka, Aldrich, USA) and ground in a wet-pulveriser to a particle size of about 1 to 3 mm. Portions of in each case 0.43 g of the mixture are then transferred to soft gelatine capsules by means of a capsule-filling machine.

Example 18: Gel Formulation

An ointment formulation was tested during a pilot clinical study with 4 volunteers with psoriatic skin disorders. The components are given in grams per 100 g.

| Compound                         | Content |
|----------------------------------|---------|
| para-topolin mesylate salt       | 1.0 g   |
| Butylhydroxytoluenum             | 0.2 g   |
| Butylparaben                     | 0.2 g   |
| Diethyleneglycol monoethyl ether | 10.0 g  |
| Silica colloidalis anhydrica     | 5.0 g   |
| Propylene glycol laurate         | 83.6 g  |

The gel consistence may be additionally modified by addition of silica colloidalis anhydrica. It is again expected that the transdermal Transcutol P/Lauroglycol FCC system will increase the efficiency of para-topolin mesylate salt. Silica colloidalis anhydrica will probably slow down the penetration of the active substance.

Example 19: Preparation Procedure of a Skin Ointment

The formulation components are given in grams per 200 g:

| Compound                         | Content  |
|----------------------------------|----------|
| para-topolin mesylate salt       | 2.0 g    |
| Butylhydroxytoluenum             | 0.4 g    |
| Butylparaben                     | 0.4 g    |
| Diethyleneglycol monoethyl ether | 20.0 g   |
| Glycerol dibehenate              | 44.0 g   |
| Propylene glycol laurate         | 133.2 g  |

Recommended Procedure

Phase A: 2 grams of para-topolin mesylate salt were dissolved in 20 g of Transcutol P while stirring continuously at room temperature in a separate glass or stainless-steel container. The dissolution process may be accelerated by heating the solution to a maximal temperature of 40° C.

Phase B: 0.4 grams of Nipanox BHT and 0.4 g of Nipabutyl were dissolved while stirring continuously in 133.2 g of Lauroglycol FCC at a temperature of approximately 70° C. in another separate glass or stainless-steel container. The clear oily solution is heated to a temperature of approximately 80° C. and 44 g of Compritol 888 ATO are melted in it while stirring continuously. The clear oily solution is cooled down to approximately 60° C. and during continuous stirring and cooling down is mixed with phase A. The resulting whitish ointment-like substance is divided into approximately 15 gram portions and filled into prearranged plastic containers.

Example 20: Formulation of a Composition for Topical Application to the Skin A composition for topical application to the skin contains the following ingredients by weight %:

| | | |
|---|---|---|
| Active ingredient: | para-topolin mesylate | 0.1% |
| Oil phase: | Cetyl alcohol | 5.0% |
| | Glyceryl monostearate | 15.0% |
| | Sorbitan monooleate | 0.3% |
| | Polysorbate 80 USP | 0.3% |
| Aqueous phase: | Methylcellulose 100 cps | 1.0% |
| | Methyl paraben | 0.25% |
| | Propyl paraben | 0.15% |
| | Purified water q.s. to 100% | 77.9% |

Methyl paraben and propyl paraben were dissolved in hot water and subsequently methylcellulose was dispersed in the hot water. The mixture was chilled at 6° C. until the methylcellulose dissolved. The mixture was then heated to 72° C. and added to the oil phase which was heated to 70° C. while stirring continuously. Para-topolin mesylate salt was added at a temperature of 35° C. and the resulting mixture was stirred continuously until dispersed. This composition is applied to the skin on at least a daily basis until the desired skin-ameliorating (anti-aging) effect is reached.

The invention claimed is:

1. Crystalline form of 6-(4-hydroxybenzylamino) purinium mesylate characterized by an CuKα X-ray powder diffraction pattern having characteristic peaks at 9.0; 9.2; 17.0; 17.9; 18.1; 22.3; 22.4; 24.1; 26.4±0.2° 2-theta.

2. Crystalline form according to claim 1, having further characteristic peaks in the X-ray powder diffraction pattern measured by CuKα radiation: 13.6; 15.6; 16.3; 16.7; 19.8; 25.7; 27.2±0.2° 2-theta.

3. A method of treatment, comprising the step of administering a medicament comprising the crystalline form of 6-(4-hydroxybenzylamino) purinium mesylate according to claim 1 to a subject in need thereof.

4. A method of treatment or improvement of a condition, comprising the step of administering the crystalline form of 6-(4-hydroxybenzylamino) purinium mesylate according to claim 1 to a subject in need thereof, wherein the condition is selected from the group consisting of skin disease, skin condition, neurodegenerative disease, immunostimulation and inflammation.

5. A method of prevention and/or treatment of a disease or condition, comprising the step of administering the crystalline form of 6-(4-hydroxybenzylamino) purinium mesylate according to claim 1 to a subject in need thereof, wherein the disease or condition is selected from the group consisting of skin cancer, psoriasis, fibrotic disorders, scleroderma, graft versus host disease (GVHD), hypertrophic scars, nephrogenic systemic fibrosis, allergic eczema, toxic eczema, atopic dermatitis, lichen planus, hyperpigmentation and herpes simplex lesions, ichthyosis, papilloma, Bowen's disease, seborrheic keratoses, actinic keratoses, basal and squamous cell carcinoma, arthritis, transplant rejection, pain, erythrema and redness.

6. A method of prevention and/or treatment, comprising the step of administering the crystalline form of 6-(4-hydroxybenzylamino) purinium mesylate according to claim 1, as a cosmetic active ingredient, to a subject in need thereof.

7. The method of prevention and/or treatment according to claim 6, wherein the treatment is selected from the group consisting of rejuvenating cells and tissues; improving the overall appearance and condition of skin; improvement in acne and/or erythema; reduction of redness; reducing number and/or depth of wrinkles and/or lines; improvement of a condition selected from the group consisting of sagging skin, discoloration, appearance of age spots, leathery and/or yellowed areas of skin; and improving the cosmetic appearance of skin.

8. A method of prevention and/or treatment, comprising the step of administering the crystalline form of 6-(4-hydroxybenzylamino) purinium mesylate according to claim 1 to a subject in need thereof, the method comprising administration in a context selected from the group consisting of in vitro for rejuvenating cells and tissues, stimulating cell proliferation, morphogenesis and/or differentiation, inhibiting cell aging and inhibiting tissue aging.

9. A cosmetic and/or pharmaceutical composition, characterized in that it comprises the crystalline form of 6-(4-hydroxybenzylamino) purinium mesylate according to claim 1 and at least one cosmetically and/or pharmaceutically acceptable excipient.

10. A method of treatment or improvement of skin disease, skin condition, or neurodegenerative disease, said method comprising administering the crystalline form of 6-(4-hydroxybenzylamino) purinium mesylate according to claim 1 to a subject in need thereof.

11. A method for suppression of immunostimulation or inflammation, said method comprising the step of administering the crystalline form of 6-(4-hydroxybenzylamino) purinium mesylate according to claim 1 to a subject in need thereof.

12. A method of prevention and/or treatment of a disease and/or condition, wherein the disease and/or condition is selected from the group consisting of skin cancer, psoriasis, fibrotic disorders, scleroderma, graft versus host disease (GVHD), hypertrophic scars, nephrogenic systemic fibrosis, allergic eczema, toxic eczema, atopic dermatitis, lichen planus, hyperpigmentation and herpes simplex lesions, ichthyosis, papilloma, Bowen's disease, seborrheic keratoses, actinic keratoses, basal and squamous cell carcinoma, arthritis, transplant rejection, pain, erythrema and redness, said method comprising the step of administering the crystalline form of 6-(4-hydroxybenzylamino) purinium mesylate according to claim 2 to a subject in need thereof.

13. A method for achieving a therapeutic outcome, the therapeutic outcome selected from the group consisting of rejuvenating the cells and tissues; improving the overall appearance and condition of the skin; improvement in acne and/or erythema; reduction of redness; reducing number and/or depth of wrinkles and/or lines; improvement of a condition selected from the group consisting of sagging skin, discoloration, appearance of age spots, leathery and/or yellowed areas of the skin; and improving cosmetic appearance of skin, said method comprising administering the crystalline form of 6-(4-hydroxybenzylamino) purinium mesylate according to claim 1 to a subject in need thereof.

14. A method of prevention and/or treatment, the method comprising administration in a context selected from the group consisting of in vitro rejuvenating cells and tissues, stimulating cell proliferation, morphogenesis and/or differentiation, inhibiting cell aging and inhibiting tissue aging, said method comprising applying the crystalline form of 6-(4-hydroxybenzylamino) purinium mesylate according to claim 1 to cells and/or tissues.

* * * * *